United States Patent [19]

Osband

[11] Patent Number: 5,192,537
[45] Date of Patent: Mar. 9, 1993

[54] METHOD OF TREATING RENAL CELL CARCINOMA USING ACTIVATED MONONUCLEAR CELLS, RENAL TUMOR ANTIGEN AND CIMETIDINE

[75] Inventor: Michael E. Osband, Brookline, Mass.

[73] Assignee: Cellcor Inc., Newton, Mass.

[21] Appl. No.: 747,484

[22] Filed: Aug. 19, 1991

Related U.S. Application Data

[63] Continuation of Ser. No. 681,668, Apr. 8, 1991, abandoned, which is a continuation of Ser. No. 405,044, Sep. 11, 1989, abandoned, which is a continuation of Ser. No. 903,489, Sep. 4, 1986, abandoned, which is a continuation-in-part of Ser. No. 595,081, Mar. 30, 1984, abandoned.

[51] Int. Cl.$^5$ .................. A61K 45/05; A61K 39/00; A01N 63/00; A01N 43/24
[52] U.S. Cl. .................. 424/85.2; 424/88; 424/93 R; 424/534; 514/2; 514/339; 514/482
[58] Field of Search .................. 424/85.2, 85.02, 88, 424/93 R, 534; 514/339, 482, 2

[56] References Cited

U.S. PATENT DOCUMENTS

| | | | |
|---|---|---|---|
| 4,404,280 | 9/1983 | Gillis | 435/68 |
| 4,444,887 | 4/1984 | Hoffman | 435/240 |
| 4,690,915 | 9/1987 | Rosenberg | 514/2 |
| 4,716,111 | 12/1987 | Osband et al. | 435/68 |

FOREIGN PATENT DOCUMENTS

87/00054 4/1987 PCT Int'l Appl. .

OTHER PUBLICATIONS

Osband et al "Successful Tumor . . . " *The Lancet* Mar. 21, 1981, vol. 1:636-638.

Palacios "Cimetidine . . . " *Immunol. Lett.* 3(1):33-37 (1981).

Berken "Case for Adoptive Immunotherapy in Cancer" *Lancet* Nov. 27, 1982 pp. 1190-1192.

Strausser et al. *J Imm* vol. 127 pp. 266-271 1981 "Lysis of human solid tumors by autolayer cells sensitized in vitro to alloantigens".

Lotze et al. *Cancer Res* vol. 41 Nov. 1981 pp. 4420-4426 "Lysis of fresh and cultured autolayer tumor by human lymphocytes cultured in T cell growth facter".

Palacios et al. *Chem Abst* 1981 vol. 95(5) No. 35349j "Cimetidine abrogaates suppressor T cell function in vitro".

Mazumder et al. *Chem Abst* vol. 96(23) No. 197,727d "Lysis of fresh human solid tumors by autolayer lymphocyles activated in vitro with lectins".

Lotze et al. *Biol Abst.* 73:84574 (1981).

Hoffman *Proc. Natl. Acad. Sci. USA* vol. 77, No. 2, pp. 1139-1143, Feb. 1980.

Oppenheim et al. *Basic & Clinical Immunology* pp. 86-90, 1984.

Frenster *The Lancet* pp. 979-980, Nov. 2, 1968.

Suciu-Foca et al. *Chem. Abst.* 80(15):80827q 1972.

*Primary Examiner*—Frederick E. Waddell
*Assistant Examiner*—Gregory Hook
*Attorney, Agent, or Firm*—Nixon & Vanderhye

[57] ABSTRACT

Immunoreactive cells sensitized for an antigenic marker associated with a malignant tumor are prepared in vitro by collecting the tumor patient's own mononuclear cells, depleting suppressor T-cells, suspending the mononuclear cells with serum, preferably autologous, and culturing the cells under conditions to activate and immunize the patient's mononuclear cells against the patient's tumor. Methods of treatment and immunized cells in pharmaceutical presentations are described.

5 Claims, 1 Drawing Sheet

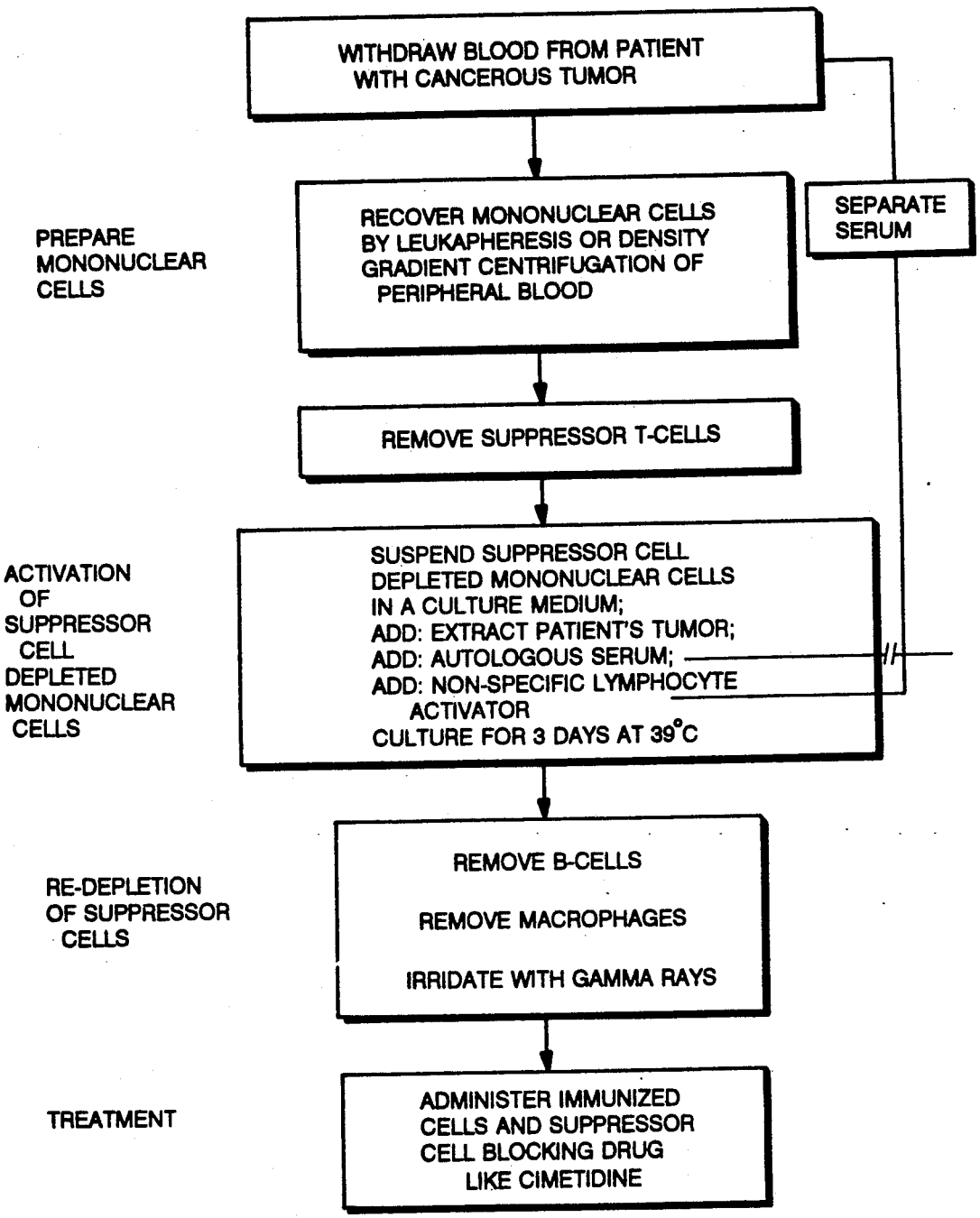

METHOD OF TREATING RENAL CELL CARCINOMA USING ACTIVATED MONONUCLEAR CELLS, RENAL TUMOR ANTIGEN AND CIMETIDINE

CROSS REFERENCE TO RELATED APPLICATIONS

This is a continuation of application Ser. No. 07/681,668, filed Apr. 8, 1991, which is a continuation of application Ser. No. 07/405,044, filed Sep. 11, 1989, which is a continuation of application Ser. No. 06/903,489, filed Sep. 4, 1986, which is a continuation-in-part of application Ser. No. 06/595,081, filed Mar. 30, 1984, all now abandoned.

BACKGROUND OF THE INVENTION

This invention relates to a process for treating a patient having a malignant tumor by activating human blood mononuclear cells of the patient and infusing them back into the patient.

A type of cancer treatment, termed adoptive immunotherapy, is based on the infusion into the patient of immunoreactive lymphocytes that generate an anti-tumor immune response. Unfortunately, the toxicity that accompanies the conventional approach to this therapy is substantial, and in combination with the high cost, raises serious doubts concerning the feasibility and practical application of this treatment. We have developed a novel approach to adoptive immunotherapy in order to make it a more feasible and cost-effective treatment. Our approach to adoptive immunotherapy is based upon the effective specific immunization of the patient by the tumor through the in vitro immunization of the patient's own peripheral blood lymphocytes followed by the infusion back into the patient of these in vitro immunized cells. In vitro immunization can be more effective than conventional in vivo immunization since it allows for the tight control of several variables that might be critical to the immunization process, including antigen concentration, duration of antigen exposure, method of antigen presentation, depletion or enrichment from within the total population of cells to be immunized of various lymphocyte subsets and the presence of lymphokines and other immunomodulators in the immunizing cultures.

In U.S. patent Ser. No. 407,236, filed Aug. 11, 1982, now abandoned and its continuation Ser. No. 696,546 filed Jan. 30, 1985, now U.S. Pat. No. 4,711,611 both by Osband et al., a procedure is disclosed for producing antibodies and immunoreactive lymphocytes by exposing in vitro the mononuclear cells of a patient to an antigen to which the patient had not been exposed previously (primary immunization). While methods have been described previously which allow for the immunization of mononuclear cells to an antigen to which the person was exposed previously (secondary immunization), the process for primary in vitro immunization that is described in these applications is optimal as well for secondary immunization/activation, and the cells that result are suited for subsequent therapeutic use by their infusion into the patient.

It would be highly desirable to provide a process for producing immunoreactive lymphocytes against a patient's tumor that does not threaten the patient's health. Furthermore, it would be desirable to provide such a process in which continuous cell lines can be formed so that cell or cell products, including antibody, can be obtained continuously over a long period of time so that the patient can be treated with the cells or cell products.

SUMMARY OF THE INVENTION

In accordance with this invention, the peripheral blood lymphocytes of a patient afflicted with a cancer are treated to activate their responsiveness to an antigen(s) associated with the tumor. Mononuclear cells are first obtained, for example, from the patient's peripheral blood. The suppressor T-cells then are removed and the remaining cells are suspended in a tissue culture medium containing a non-specific lymphocyte activator, preferably also with an extract of the patient's tumor, and preferably also with the patient's own (autologous) serum. The cells then are incubated, preferably under hyperthermic conditions, for a period of time so that they are activated against the patient's tumor. It is desirable that after in vitro immunization the activated cells are subjected to one or more additional procedures to re-deplete various kinds of suppressor cells, including macrophages, to additionally boost their activity. The activated cells then are administered to the patient in order to reduce or eliminate the tumor or to reduce or eliminate recurrences of the cancer. Although the infusion of in vitro immunized cells may lead to an anti-tumor immune response, it is possible that the concurrent presence of in vivo suppressor cells in the patient will block that response from being effective. Therefore, a second necessary component of our immunotherapy is a treatment with a drug that will decrease in vivo suppressor cell activity. For this purpose, we prefer to use cimetidine as the in vivo suppressor cell blocker. Although developed as an anti-ulcer drug, cimetidine has proven anti-suppressor cell activity in both tumor and non-tumor settings in both man and animal. It is orally administered and therefore convenient for patients to take, and it is a relatively safe drug even when used for extended periods of time.

Antigen-specific immunoreactive lymphocytes produced by this novel process are part of the present invention, as are pharmaceutical compositions containing such cells or cell products, and their use in the treatment of a malignant tumor to which the cells or cell products are responsive. Sensitized, activated, antigen specific cells in concentrated form are also disclosed.

Tumor types amenable to treatment according to this invention include renal cell carcinoma, colo-rectal carcinoma, pancreatic carcinoma, melanoma and non-small cell carcinoma of the lung. In addition, other forms of tumors not treatable by conventional forms of therapy may be usefully approached according to the procedures of this invention.

BRIEF DESCRIPTION OF THE DRAWING

The attached FIGURE is a flow chart depicting the preferred operative steps of preparing the activated and immunized mononuclear cells specific for a patient's tumor. It will be understood that all of the steps listed are not required for the successful operation of the process.

DETAILED DESCRIPTION OF SPECIFIC EMBODIMENTS

In the process of this invention, mononuclear cells are obtained from the peripheral blood of a patient having a tumor. An additional portion of the blood sample is utilized to provide a source of autologous serum. The mononuclear leukocytes may be obtained from the patient in a number of ways, including the known techniques of leukapheresis and/or density gradient centrifugation of peripheral blood that has been anticoagulated, diluted with a physiologically acceptable solution such as saline, and layered on a centrifugation separation medium such as Ficoll-Hypaque (Pharmacia).

The suppressor T-cells then are removed by contacting the mononuclear cells with an agent having a specific affinity for these cells. A particularly suitable composition for depleting the mononuclear cells of suppressor T-cells is (1) an H2 receptor antagonist, such as cimetidine, either linked or conjugated to a macromolecule such as human albumin or albumin that has been modified by its previous conjugation to citric acid in order to maintain an appropriate net charge on the resultant macromolecule, or (2) an antibody directed against an antigen expressed on human suppressor T-cells, such as OKT8,(Ortho) or Leu-2A (Becton-Dickinson). Utilizing human albumin linked to cimetidine provides the capability of removing only those cells bearing the histamine H2 type receptor on their surface so that the non-adherent cells are greatly depleted of suppressor T-cells.

The mononuclear cells depleted of suppressor T-cells then are suspended in a culture medium to which is added (a) heat-inactivated autologous serum (previously prepared), and (b) a non-specific lymphocyte activator, and also preferably (c) antigenic components of the tumor. By this procedure, the suppressor cell depleted mononuclear cells are activated with regard to the tumor associated antigen.

If tumor associated antigen is utilized, the amount ranges between about 0.001 μg/ml and about 10 μg/ml and can be lesser or greater in certain specific instances. It is to be understood that the optimal amount of the tumor associated antigen to be utilized employing the techniques of this invention can easily be determined through trial and error merely by measuring the quantity of antibody or the degree of T-cell activation in the activation culture. Alternatively, the suppressor cell depleted mononuclear cells may be incubated with a macrophage monolayer that is optionally previously pulsed with tumor associated antigens. Although it is preferable, it is not necessary to employ tumor associated antigen within the immunizing culture, which in some cases is difficult to obtain, since the mononuclear cells have been previously exposed to tumor associated antigens within the patient's body.

It is best to utilize heat-inactivated autologous serum in the immunizing culture rather than serum obtained from another human (i.e., allogenic serum) or non-human animal (i.e., xenogenic serum) in accordance with this invention. It is believed that autologous serum is necessary for optimal activation of the particular patient's mononuclear cells. The amount of autologous serum utilized is generally between about 2 and 15% of the culture medium.

In each culture medium, the concentration of mononuclear cells can be varied between about 0.5 and about $5.0 \times 10^6$ cells/ml. A concentration of about $1.0 \times 10^6$ cells/ml is most preferred. Any standard tissue culture medium can be utilized in the process of this invention including RPMI 1640 available from M. A. Bio-Products.

A non-specific lymphocyte activator is used in the process and representative suitable activators include phytohemagglutinin (PHA), interleukin 1 (IL-1), interleukin 2 (IL-2), pokeweed mitogen (PWM), supernatants from cultures of human mononuclear cells stimulated with PHA, PWM, IL-1 or IL-2 or the supernatant of a mixed lymphocyte culture (MLC) obtained by incubating responding human cells against irradiated allogeneic stimulator cells. These conditioned supernatants obtained from an MLC, or from culturing human mononuclear cells with PHA, PWM, IL-1 or IL-2 can be utilized in the final culture medium in an amount of between 0 and 50%, preferably between about 20 and 33%. The conditioned supernatants can be used immediately or stored frozen at −20° C. and then thawed for use in the activating/immunizing cultures. The conditioning culture goes on about 24 to about 60 hours prior to collecting the supernatant. The optimal concentration of PHA, PWM, IL-1 or IL-2 can vary from lot to lot and manufacturer to manufacturer. Therefore, all that one needs to do is to test each lot and optimize each batch of material prior to utilizing it in volume. These non-specific activators can be used alone or in various combinations.

The activated and immunized cells so prepared may be infused back into the patient or further enriched in activity by a re-depletion of suppressor cells. This supplemental depletion of certain suppressor cells following the in vitro immunization is accomplished in any one of the following ways, preferably all three. They are: (1) depletion of B-cells, for example, using an anti-antibody (the B-cells, although immunized, are not necessary to the clinical anti-cancer effect), (2) depletion of macrophages, for example, by allowing them to adhere to a plastic surface, and (3) depletion of radiosensitive suppressor cells by treating the immunized cells with low dose gamma irradiation, for example, in the range of 50–400 rad. Cells that undergo this additional depletion of suppressor cells were found to be significantly more active than in the absence of the re-depletion step or steps, and for this reason these steps are highly desirable.

The cells are incubated at 37° C. or preferably under hyperthermic conditions at a temperature in the range of 38° to about 41° C., preferably 39° C.. At the end of the activating culture, generally around 3 days, the patient's activated and immunized lymphocytes can be infused back into the patient. The number of cells infused at one time can range between about $1.0 \times 10^7$ and $1 \times 10^{11}$ suspended in an appropriate amount (about 50–100 cc) of an injectable carrier, such as normal saline. At predetermined intervals such cultures are prepared and infused into the patient. Cell cultures are prepared periodically prior to each infusion. Six infusions spaced one month apart appears to be best, but this may vary from patient to patient and can be adjusted in accordance with the clinical response. It is surprising that this number of activated cells, relatively small as compared to the number of mononuclear cells in the patient's blood, can effect an in vivo response which is therapeutic for the patient as shown by the results in the examples below.

In order to improve the efficacy of these activated and immunized cells when infused into the cancer-bearing patient's body, it is desirable to inactivate the suppressor cells already present in the patient. For this purpose, the patient may be receiving, throughout the duration of this treatment, a drug, such as cimetidine, which has been shown to block the H2 histamine receptor and thereby inhibit the patient's suppressor cells. Other agents similarly useful may be indomethacin, or a monoclonal antibody directed against suppressor cells. This blocking of in vivo suppressor cells may subsequently enable the activity of the infused in vitro activated cells to be amplified. The combination of these suppressor cell depleted lymphocytes that were specifically immunized in vitro against tumor antigen under the conditions described above together, with a drug such as oral cimetidine that blocks the activation of suppressor cells in vivo that may interfere with the effect of the immunized cells, offers a novel and significant improvement over other methods of adoptive immunotherapy.

Also, the sensitized lymphocyte cells (both T- and B-cells) that are reactive against the patient's tumor can be immortalized by any conventional means such as by exposure to Epstein-Barr virus, by conventional fusion to myeloma cells with the well-known procedure of Kohler and Milstein or fusion with other immortal cell lines, including T-cell lines.

This invention will be most useful for those neoplasia that are not responsive to other forms of therapy, and who share certain biological attributes, including the kinetics of their growth, and relationship to the patient's immune system. This includes tumors of the gastrointestinal tract (such as colorectal carcinoma), pancreatic carcinoma, non-small cell lung carcinoma, renal cell carcinoma, tumors of the central nervous system (such as glioblastoma) and melanoma.

The following examples illustrate the present invention and are not intended to limit the same.

EXAMPLE 1

Culture medium A: RPMI 1640 medium containing 100% autologous serum (v/v, obtained from the patient from a previous venipuncture, heat inactivated at 56° C. for 30 minutes and stored at −20° C. until use) and 25% (v/v) supernatant from a mixed lymphocyte culture (prepared as described below). In addition, culture medium B is supplemented with Hepes buffer 0.025 M, glutamine 0.002 M, penicillin (1 unit/ml) and streptomycin (1 µg/ml).

Culture medium B: RPMI 1640 5% autologous serum (v/v) and supplemented as in A, above.

Production of Mixed Lymphocyte Culture Supernatant

1. Autologous peripheral blood mononuclear cells were obtained as set forth above.
2. They are resuspended in culture medium B at $2 \times 10^6$ cells/ml.
3. Allogeneic peripheral blood mononuclear cells were obtained, resuspended at $2.0 \times 10^6$ cells/ml in culture medium B and irradiated with 3000 rad.
4. Responder (autologous to the immunization donor) and stimulator (the allogeneic source) cell suspensions are mixed 1:1 vol/vol.
5. The final cell suspension ($2 \times 10^6$ cells/ml composed of $1 \times 10^6$ cells/ml each of responder and stimulator cells) was cultured for 48 hours at 37° C. in a moist-air incubator containing 5% $CO_2$.
6. At 48 hours, the culture is centrifuged to pellet the cells and the supernatant used immediately or frozen at −20° C. until thawed and used.

Production of Tumor Associated Antigen

1. A portion of the patient's tumor, previously isolated, is homogenized in a Waring blender at 4° C.. Ten ml of phosphate buffered saline (PBS), pH 7.2, is used per gram of tumor tissue. About 5 gm of tumor tissue is homogenized and extracted at one time.
2. The blender is run intermittently for about 2 minutes so as not to heat the homogenate excessively.
3. The homogenate is centrifuged for 10 minutes at $200 \times g$ to remove particulate matter and cellular debris.
4. The resultant supernatant is centrifuged further for 20 minutes at $20,000 \times g$ to form a pellet.
5. The resultant pellet containing cell membranes is resuspended in 50 ml of 3 M KCl and rocked for 18 hours at 4° C.
6. The mixture is then ultracentrifuged for 1 hour at $100,000 \times g$ at 4° C.
7. The supernatant containing dissolved protein and other membrane-derived molecules is collected and dialyzed $\times 3$ for 30 minutes each at 4° C. a 200-fold volume of PBS
8. The material is then sterilized by passage through a 0.45 uM filter and either used immediately or stored at −20° C. until use.

Immunization Process

The following represents the process used to immunize in vitro human cells against antigen associated with renal cell carcinoma.

1. 400 cc of peripheral venous blood was collected in preservative-free heparin from the patient afflicted with the renal carcinoma carcinoma.
2. The blood was diluted 1:1 with normal saline and layered on Lymphocyte Separation Medium (2:1 blood mixture to LSM), and centrifuged at $800 \times g$ for 20 minutes at room temperature.
3. The interface cells were collected, washed and resuspended at $3–10 \times 10^7$/ml in phosphate-buffered saline, p.H 7.2, containing 7.5% heat inactivated fetal bovine serum.
4. The cells were layered onto a petri dish coated with human serum albumin-cimetidine and incubated at 37° C. for 60 minutes. At that time, the petri dish was swirled gently and the medium poured off. The plate was washed $\times 1$ by swirling gently with 10 ml of PBS and poured off. These two pour-offs contain the suppressor T-cell depleted population. These cells were washed twice in HBSS and resuspended in culture medium B to which was added the tumor extract to a final concentration of 0.1 µg/ml.
5. The cells were cultured at 39° C. in a moist-air incubator with 5% $CO_2$ at a density of $2 \times 10^6$ cells/ml in Culture Medium A. After 3 days in culture the immunized autologous lymphocytes ($100–200 \times 10^6$ cells) were washed and infused back into the patient.

EXAMPLE 2

In this example the effects were studied of autologous human peripheral blood mononuclear cells that had been specifically immunized in vitro against autologous tumor antigen together with orally administered cimetidine to block the activation of suppressor cells in vivo that might block the effect of the immunized were studied. Procedures for preparing the in vitro immunized cells are similar to those described above.

A clinical trial of adoptive immunotherapy was conducted in 20 patients with metastatic renal cell carcinoma, a form of cancer unresponsive to traditional forms of treatment. Patients peripheral blood mononuclear cells (PBM) were depleted of suppressor T cells and immunized in vitro against an autologous tumor antigen extract in the presence of a non-specific lymphocyte activator as described in detail below. After one week in culture the in vitro immunized cells were infused back into the patient. Each patient received a total of three infusions, delivered at weekly intervals, of $50-150 \times 10^6$ cells per infusion. In addition, all patients were treated with oral cimetidine, 600 mg four times a day, as an anti-suppressor cell agent. A total of 60 immunized cell infusions were given to the 20 patients and no serious technical problems were encountered with this therapy.

A specimen of tumor tissue, weighing at least 5 grams, was obtained from each patient being treated, either at the time of initial surgery or by subsequent biopsy. Autologous tumor antigen was prepared using the procedure in of Example 1. Mixed lymphocyte culture supernatant (MLC-S) for use as a non-specific lymphocyte activator was prepared using the procedure in Example 1.

Patient peripheral blood mononuclear cells (PBM) were depleted of H2 histamine receptor suppressor T-cells (H2R+cells) by "panning" the cells on a petri dish coated with human albumin conjugated to cimetidine (Cell-ect H2 kit, Clinical Immunology, Inc., Boston, Ma.). In order to determine the optimal concentration of tumor antigen extract to use in the in vitro immunizing cultures, a screening culture was performed in which aliquots of $2 \times 10^6$ suppressor cell-depleted PBM were dispensed into culture tubes in the presence of serial logarithmic concentrations of autologous tumor extract (final protein concentration $10^{-4}$ to $10^2$ ug/ml). Following incubation for 7 days the cultures were harvested and the supernatants assayed by standard ELISA technique for tumor extract-specific antibody. For each patient, the concentration of tumor extract that elicited the highest anti-tumor antibody levels in the culture supernatants was subsequently chosen for use in that patient's in vitro immunizing cultures.

Preparation of in vitro immunized autologous PBM suppressor cell-depleted PBM were obtained as described above and suspended at $2 \times 10^6$ cells/ml in culture medium RPMI 1640 containing the previously determined optimal concentration of autologous tumor extract and 10% heat-inactivated autologous serum. In addition, all cultures were supplemented with a non-specific lymphocyte activator, either 25% MLC-S (Patients #1-8 and 17-20) or pokeweed mitogen (Patients #9-16). Following incubation for 7 days at 37° C. in a moist air incubator containing 5% $CO_2$, the cells were harvested, washed extensively and resuspended at $2 \times 10^6$ cells/ml in sterile, non-pyrogenic normal saline containing 5% heat-inactivated autologous serum. All immunizing cultures to be used for infusion were evaluated microscopically for the presence of pathogens. In addition, they were Gram stained and cultured for pathogens prior to infusion of the cells.

Infusion of immunized cells: a preliminary test dose of $1 \times 10^6$ autologous immunized PBM in 0.5 ml was infused intravenously over 5 minutes via an angiocatheter to which was attached a standard blood administration filter. If no adverse reaction was seen, the remainder of the cells were infused over the ensuing 30 minutes. Vital signs were monitored before and after the infusion. Beginning one week prior to the first cell infusion, patients began receiving cimetidine orally, 600 mg four times per day.

Complete history and physical examination, hematologic, serum chemistry and coagulation studies, urinalysis and all relevant imaging studies needed to evaluate the extent of a patient's metastatic disease, were performed prior to the first cell infusion. These were repeated at regular intervals after the first infusion of cells to evaluate the safety and efficacy of the treatment. Tumor lesions were measured as the product of the greatest two perpendicular diameters. Clinical responses were based on the sum of all tumor lesions and categorized using standard oncologic definitions.

The results are given in Table 1. The total number of immunized cells that were infused in each patient ranged from $1.5-4.4 \times 10^8$ cells, as indicated. Toxicity was minimal consisting only of four episodes of fever that occurred in three patients following the infusion of immunized PBM. No other adverse reactions or complications were seen in the treated patients, there was no evidence in the treated patients of any adverse reaction that could be described as autoimmune, hyperimmune or relating to the formation of immune complexes, and there was no evidence that this therapy worsened or hastened the natural course of disease in the treated patients.

Fourteen of the 20 patients treated with this protocol were evaluable with regard to clinical responsiveness (excluding 6 patients who were in a terminal state at the time of entry to the study and subsequently expired prior to first evaluation). Nine of the 14 evaluable patients (64%) had an objective clinical response to therapy. Three patients had a partial response (decrease of >50% in the sum of all lesions without appearance of new disease). The duration of these partial responses was as long as 18 months in two patients, one of which is still on-going at 36 months. Two others had tumor regresssion (decrease >25% but <50% in the sum of all lesions as evaluated by two independent investigators, without appearance of new lesions). In addition, four other patients demonstrated stable disease for long periods of time, after previously showing rapid growth of their tumor.

TABLE 1

| Patient No. | Age at Entry | Sex | Sites of Metastases | Total # of Cells $\times 10^8$ | Survival in months after treatment | Clinical Response |
|---|---|---|---|---|---|---|
| 1 | 57 | M | brain, liver, lungs, nodes | 4.4 | 25 | partial response |
| 2 | 33 | F | bone, lungs, mediastinum, nodes | 3.5 | 9 | partial response |
| 3 | 68 | M | bone, nodes, renal fossa | 2.4 | 13 | stable disease |
| 4 | 48 | M | lungs, renal fossa | 3.2 | 24* | partial response |
| 5 | 51 | F | bone, lungs, mediastinum, nodes | 1.4 | <1 | + |
| 6 | 56 | M | bone, lungs, mediastinum, subcutaneous tissue | 2.5 | .6 | tumor regression |
| 7 | 63 | M | liver, lungs, pelvis | 2.2 | 15 | stable disease |
| 8 | 62 | M | bone, renal fossa | 1.5 | 19* | stable disease |
| 9 | 40 | M | bone, lungs, mediastinum, sacrum | 1.7 | 7 | no response |
| 10 | 52 | F | brain, mediastinum | 1.7 | 2.5 | + |
| 11 | 48 | M | bone, brain, lungs, renal fossa | 3.1 | 8 | no response |
| 12 | 60 | F | liver | 2.0 | 12 | stable disease |
| 13 | 54 | F | bone, liver, lungs, nodes, pleura | 2.4 | <1 | + |

TABLE 1-continued

| Patient No. | Age at Entry | Sex | Sites of Metastases | Total # of Cells × 10⁸ | Survival in months after treatment | Clinical Response |
|---|---|---|---|---|---|---|
| 14 | 62 | M | kidney, nodes, pancreas, retroperitoneum | 1.9 | 12 | no response |
| 15 | 52 | F | liver, lungs, mediastinum, renal fossa | 1.6 | 4 | no response |
| 16 | 44 | F | lungs, nodes, renal fossa | 2.2 | 12* | tumor regression |
| 17 | 60 | F | bone, lungs, retroperitoneum | 1.9 | 2 | + |
| 18 | 71 | M | lungs, nodes, renal fossa | 1.8 | 7 | no response |
| 19 | 61 | M | lungs, nodes | 2.4 | 1.5 | + |
| 20 | 46 | M | bone, lungs, pleura | 1.8 | 1 | + |

*currently alive
+ died prior to first evaluation timepoint

The results of this study are encouraging and demonstrate good patient acceptance, minimal toxicity and a positive clinical response to a form of cancer that is unresponsive to traditional forms of therapy.

Other embodiments of the invention will be apparent to one skilled in the art from a consideration of the specification or the practice of the invention disclosed herein. It is intended that the specification and examples be considered as exemplary only, with the true scope and spirit of the invention being indicated by the appended claims.

What is claimed:

1. A method of treating renal cell carcinoma comprising administering to a patient having same an effective, renal cell carcinoma-inhibiting amount of the immunoreactive, sensitized cells and administering to the patient an amount of cimetidine effective to inhibit the patient's suppresor cells wherein said immunoreactive, sensitized cells are prepared by a process comprising the steps of:
(a) collecting mononuclear cells from the blood of an individual patient afflicted with renal cell carcinoma;
(b) incubating the mononuclear cells with an effective amount of an H2 receptor antagonist and removing or chemically inactivating the suppressor T-cells from the mononuclear cells;
(c) suspending the mononuclear cells of step (b) in culture medium and admixing the suspended mononuclear cells with autologous blood serum, a non-specific lymphocyte activator and an effective amount of an extract of the patient's tumor containing antigen specific to renal cell carcinoma;
(d) culturing the admixture of step (c) under hyperthermic conditions of about 38° C. to about 41° C. in the presence of an amount of cimetidine effective to reduce suppressor cell activity for a period of time sufficient to activate and sensitize the mononuclear cells in vitro against the patient's renal cell carcinoma; and
(e) irradiating the immunoreactive, sensitized cells with an effective amount of gamma radiation to re-deplete any radiosensitive suppressor cells that may be present in the culture of activated and immunized mononuclear cells, thereby providing immunoreactive, sensitized cells specific to the patient's renal cell carcinoma.

2. The method of claim 1 in which in step (c) the non-specific lymphocyte activator is phytohemagglutinin, interleukin 1, pokeweed mitogen, supernatants of human cells stimulated with phytohemagglutinin or pokeweed mitogen, a supernatant of a mixed lymphocyte culture, or a mixture of two or more of these activators.

3. The method of claim 2 in which the activator is a combination of phytohemagglutinin, a conditioned supernatant of a mixed lymphocyte culture and interleukin 2.

4. The method of claim 2 in which the activator is the conditioned supernatant of a mixed lymphocyte culture.

5. The method of claim 1 in which up to 2.4 grams/day of cimetidine is administered.

* * * * *